(12) United States Patent
Benz et al.

(10) Patent No.: US 6,616,634 B2
(45) Date of Patent: Sep. 9, 2003

(54) ERGONOMIC SYRINGE

(75) Inventors: Philip David Benz, Tigard, OR (US); Herbert J. Semler, Portland, OR (US); Benjamin Peter Mergen, Corbett, OR (US); William Richard Huseby, Vancouver, WA (US)

(73) Assignee: Semler Technologies, Inc., Vancouver, WA (US)

( * ) Notice: Subject to any disclaimer, the term of this patent is extended or adjusted under 35 U.S.C. 154(b) by 0 days.

(21) Appl. No.: 09/957,861

(22) Filed: Sep. 21, 2001

(65) Prior Publication Data

US 2003/0060777 A1 Mar. 27, 2003

(51) Int. Cl.[7] .................................................. A61M 5/00
(52) U.S. Cl. .................................... 604/187; 222/391
(58) Field of Search .............................. 604/187, 227, 604/68, 181, 218, 235; 222/327, 391, 79

(56) References Cited

U.S. PATENT DOCUMENTS

| | | | |
|---|---|---|---|
| 1,757,809 A | * 5/1930 | Montuori | ............... 604/235 |
| 1,880,354 A | 10/1932 | Mueller | |
| 2,074,401 A | 3/1937 | Kauzal | |
| 2,316,095 A | 4/1943 | Mead | |
| 2,624,338 A | 1/1953 | Moore | |
| 2,750,943 A | 6/1956 | Dann | |
| 2,816,546 A | 12/1957 | Luhmann | |
| 2,882,901 A | 4/1959 | De Venezia | |
| D249,808 S | * 10/1978 | Bloom et al. | |
| 4,925,449 A | 5/1990 | Saez | |
| 4,968,303 A | * 11/1990 | Clarke et al. | ............... 604/187 |
| D320,276 S | 9/1991 | Baum | |
| D325,437 S | 4/1992 | Hull | |
| 5,209,731 A | 5/1993 | Sterman | |
| 5,221,348 A | * 6/1993 | Masano | ............... 118/506 |
| 5,228,883 A | 7/1993 | Blakely | |
| 5,408,919 A | * 4/1995 | Hutzler et al. | ............... 99/345 |
| 5,830,194 A | 11/1998 | Anwar | |
| 6,030,368 A | 2/2000 | Anwar | |

* cited by examiner

Primary Examiner—Michael J Hayes
Assistant Examiner—Kevin C. Sirmons

(57) ABSTRACT

The ergonomic syringe is used by an operator to inject fluid under pressure into a patient during a medical procedure, which can include angiographic procedures where catheters are used. Although said ergonomic syringe may be connected to and used with a catheter of any size, it is particularly suited for use by an operator to inject radiopaque dye through catheters having small diameters. The large handgrip and locations of the fingergrips, together with other features on these elements of the ergonomic syringe, increase comfort and reduce the fatigue, strain, and risk of disability which may be associated with achieving the force required for each injection to achieve high pressures necessary for proper dye density in the blood flow in the target blood vessels, where such force is greater in smaller catheters than in larger catheters.

9 Claims, 3 Drawing Sheets

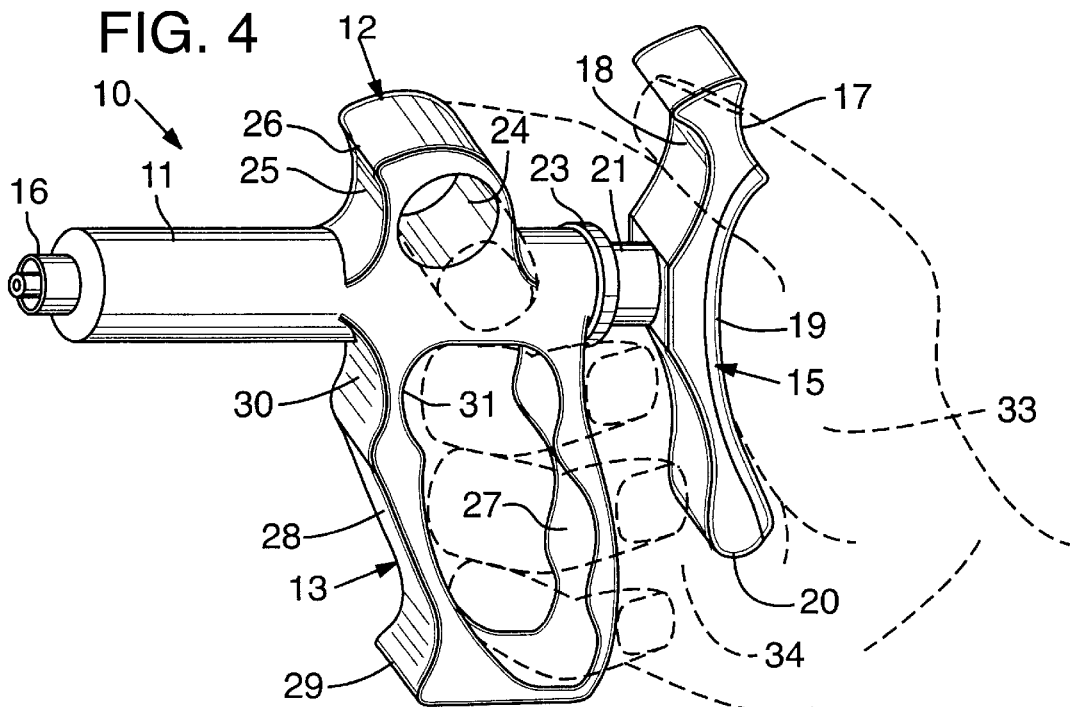
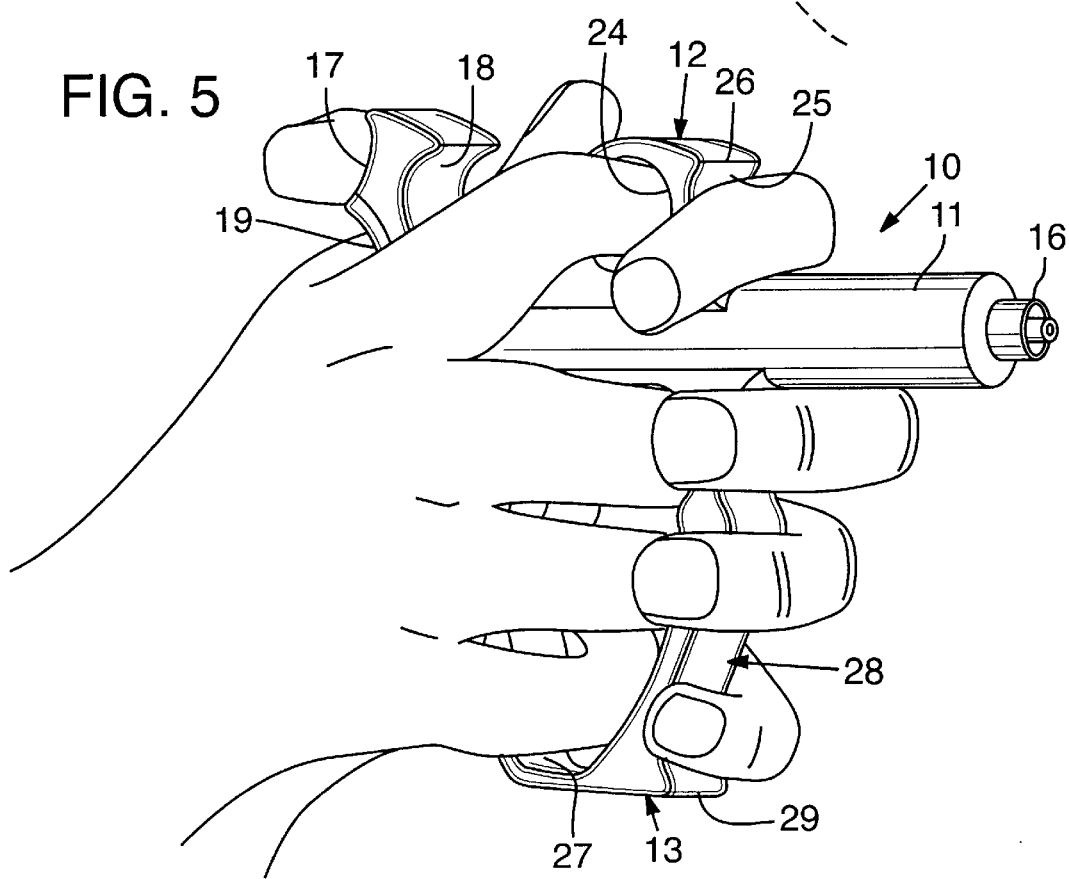

ERGONOMIC SYRINGE

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

BACKGROUND OF THE INVENTION

This invention relates to a manually-operated syringe, having ergonomic advantages, to be used in medical procedures. More particularly, an intent of this ergonomic syringe is its use for injecting radiographically opaque contrast medium into the vascular system of a patient during angiographic procedures, for the purpose of enhancing visualization of the vascular system on angiograms or other radiograms.

The radiographically opaque contrast medium, also called dye, is injected into the vascular system typically through a hollow catheter which has been inserted into a patient's artery or vein. For example, the catheter for coronary angiography is usually inserted into the femoral artery or radial artery. The open end of the catheter through which the dye is introduced into the blood flow is guided through the vascular system to the target area by the operator, normally a physician. The dye is injected through the catheter into the blood vessels being evaluated at the time that the angiogram is recorded. Because the dye is opaque to the x-rays used in angiography, it enhances the contrast on the angiogram so as to better show the interior topography of the blood vessels into which the dye is injected. A minimum density of dye in the blood flow of the vessels being evaluated is required in order for a diagnostically-useful angiogram to result. Dye normally has a higher viscosity than water or blood, with a measured viscosity, in centipoise, of between 2 and 20, where the viscosity of water is 1.

Dye is normally injected from a manually-operated syringe into an attached manifold, and therefrom into an attached catheter, these three items being in fluid communication by direct connection or by hollow tubing. The syringe, manifold, tubing, and proximal end of the catheter are located outside the patient's body. The connections between the syringe, manifold, tubing, and catheter are made using a threaded connector, typically a Luer connector. The manifold is used as a means of connecting the syringe, catheter and sources of dye and sometimes saline solution. By manipulating valves, also commonly known as stopcocks, the operator can open and close channels to the dye, saline and catheter, enabling desired fluid flow.

For coronary angiography, between six and 12 milliliters of dye are normally injected per angiogram; this injection should normally take approximately two seconds. If the injection takes substantially longer than approximately two seconds, the density of the dye in the blood flow decreases, lowering the contrast of the angiogram, thereby reducing its usefulness since the interior topography of the vessels being evaluated will not stand out sufficiently from the background of the angiogram. A catheter used for injecting dye is often also called a diagnostic catheter. Multiple injections of dye are required during each procedure, since many different angiographic views are recorded.

Operators injecting the dye normally use syringes made of plastic or polypropylene, with the barrel of the syringe held with the index and third finger placed either in rings or against flanges formed as part of the barrel, and with the plunger of the syringe actuated by the thumb. In many instances, a ring is formed as part of the end of the plunger, so as to enable forward and backward motion in response to the thumb's direction of movement. This style of syringe has been adequate to administer dye with the sizes of catheters in common use, for example, those sized 6 French or larger. French Size increments are in intervals of 0.3 millimeters; for example, a 6 French catheter has an outside diameter of 2.0 millimeters, and a 7 French catheter has an outside diameter of 2.3 millimeters. Inside diameters vary from catheter to catheter; a 6 French diagnostic catheter can be expected to have an inside diameter of approximately 1.3 millimeters, and a 7 French diagnostic catheter an inside diameter of approximately 1.6 millimeters.

Smaller catheters have been introduced because of benefits associated with the smaller puncture hole required to insert the catheters into the body; as the size of the puncture hole decreases, the risk of puncture site complications and the time required for the patient to ambulate decreases. These recently-introduced smaller diagnostic catheters, in 4 French and 5 French sizes, have narrower lumens; a 4 French catheter can be expected to have an inside diameter of approximately 1.1 millimeters and a 5 French catheter an inside diameter of approximately 1.2 millimeters. The inside diameter of a 4 French catheter can therefore be about 15% smaller than that of a 6 French catheter and about 30% smaller than that of a 7 French catheter.

The smaller inside diameters of the 4 French and 5 French catheters make manual injection of the viscous dye more difficult compared with larger catheters. This difficulty is caused by the increased amount of injection force required to propel the dye through a smaller lumen diameter to approximate the same density of dye in the blood flow as is normally achieved with larger-diameter catheters. The degree of difficulty in maintaining a minimum density of dye in the blood flow has not normally been a problem with catheters sized 6 French or larger. As lumen sizes decrease, operator hand strength becomes a limiting factor in the proper administration of dye, even when two hands are used to inject. Where the operator's hand strength is not sufficient, for example after repeated injections, lower quality angiograms result and the operator's wrist, hand and fingers become fatigued and incur a high risk of disability due to either acute or repetitive motion injury. This in turn reduces the adoption rate of the smaller diagnostic catheters, delaying realization of the benefits of lower complication risk and earlier post-procedure ambulation.

Therefore a means of injecting dye through catheters sized 5 French or smaller is needed, which reduces stress on the operator's hand, wrist and fingers while providing a density of dye in the blood flow of the vessels being evaluated sufficient for diagnostic purposes.

One approach to alleviating this problem includes the same type of manifold and catheter normally used in angiographic procedures, but which substitutes an electromechanical injector for the manually-operated syringe. Examples of such injectors are described in U.S. Pat. Nos. 6,221,045, 5,383,858, 4,854,324, 4,677,980 and 4,006,736. These injectors were initially developed for purposes of injecting the larger volume of dye into the ventricles of the heart required for ventriculography, and are operated by inputting instructions and then actuating the device, which then automatically injects the pre-set amount of dye at the pre-set flow rate. Although useful and generally safe for ventriculography, these injectors' use in angiography incurs additional risk because of the smaller tolerances involved with injecting into the much smaller volume of a blood vessel, combined with possible unplanned variation in rate or volume of dye administration. Another important disadvantage of these injectors is that, in the event of unforeseen vessel interior topography, malfunction, or inputting improper settings when injecting into a blood vessel, a rupture or other damage could occur resulting in severe adverse health outcomes including death. An additional disadvantage is the very high cost of the injectors, both for acquiring the equipment, maintaining it during its useful life, and for procuring the disposable supplies required for its operation. A further disadvantage is the injector's large size and complexity of operation.

Manually-operated syringes have not substantially changed since the introduction of the 4-French and 5-French catheters and are similar in general form and construction to that shown in U.S. Design Pat. No. 320,276. Syringes in common use for angiography purposes are generally made of a plastic or polypropylene, with the barrel of the syringe held with the index and third fingers placed either in rings or against flanges formed as part of the barrel, and with the plunger of the syringe actuated by the thumb or a small portion of the palm of the hand. In many instances, a ring is formed as part of the proximal end of the plunger, so as to enable forward and backward motion in response to the thumb's direction of movement. None of the syringes in current use feature plungers with handgrips having a large surface area over which to distribute the pressure across a large portion of the operator's hand; such pressure is caused by application of manual force required to perform the injection. Specialized means of comfortably using two hands during the injection is not typically provided. In addition, features for finger placement on currently-used syringes are not spaced to permit best application of force during injection. A threaded connection, for example a Luer connector, is provided at the nozzle of these syringes for removable connection to the manifold which in turn connects using a similar connector to the tubing and catheter. For most operators, these syringes are often proving inadequate for use with the smaller catheters because of insufficient dye density leading to low diagnostic quality of the angiogram, and in addition, because of stress and pressure on operators+ hands, wrists and fingers even when two hands are used. These types of syringes are marketed by companies examples of which include Merit Medical Systems, Inc., Boston Scientific, and DeRoyal.

A manually-driven syringe is described by Saez et al in U.S. Pat. No. 4,925,449, whereby a comparison and modification to a then-existing syringe is described. Features of this syringe include: fingergrips on two opposing sides of the barrel, each of which includes an opening to fit two fingers; a plunger with a thumbring on its head, which, in an embodiment, may be axially collapsible; the distance between the plunger head and the placement of the operator's fingers in the fingergrips being lessened as a result of the shape and location of the fingergrips and the location of the plunger head when extended. Although this syringe may represent an improvement over the then-current syringes, it has several disadvantages. A disadvantage is the requirement that two fingers be placed in each of the fingergrips, which departs from the normal current expectation of operators and the design of syringes in common use for this purpose, where only the index finger instead of the index and third fingers held together, is placed in a fingergrip. Furthermore, the head of the plunger is shown to be similar in size to the then-current syringe of which it purports to be an improvement; this small size is a significant disadvantage in that it places excessive pressure on a small portion of the palm of the operator's hand or thumb when performing the injection. Such pressure is caused by application of manual force required to perform the injection. This disadvantage is exacerbated as the force required for injecting into the 4 French and 5 French catheters is significantly greater than the force required for injecting into the size of catheters commonly in use at the time the Saez invention was patented. A further disadvantage is the noted lack of specialized means for permitting two-handed use, which therefore reduces the potential utility of the syringe by limiting the amount of force to be applied during injection to that which can be applied with only a single hand, and increases the amount of discomfort associated with the injection.

A manually-operated, mechanically-assisted power syringe is described by Anwar in U.S. Pat. No. 6,030,368, whereby a syringe is connected in a levered apparatus providing mechanical advantage to the injection action. Although providing mechanical advantage and reducing physical stresses on operators, a disadvantage of the power syringe is its relatively large size and corresponding requirement for stable, horizontal space not normally available near the catheterization procedure table. Another disadvantage is its high cost relative to other manually-operated syringes in common use, caused by the power syringe's design, size and construction. Another disadvantage is the power syringe's mode of use, which requires the operator to press down on a lever, actuating the injection action, while the power syringe lies on a flat surface near the patient; this fundamentally different operation is unfamiliar to operators who may find gauging flow rate and volume during injection more difficult.

SUMMARY OF THE INVENTION

An object of this invention, an ergonomic syringe, is to increase comfort and reduce fatigue, strain and risk of disability for operators using syringes to inject angiographic dye during catheterization procedures, particularly when catheters sized 5 French and smaller are being used.

A further object of the invention is to make injection of fluids during medical procedures easier.

An additional object of the invention is to enable acquisition of angiograms having sufficient contrast for proper diagnostic and therapeutic use.

An additional object of the invention is to reduce the cost of each syringe.

An additional object of the invention is that its usage be similar to that of manually-operated syringes commonly used in catheterization procedures.

These and other objects are achieved with the ergonomic syringe described herein. In an embodiment, the ergonomic syringe is generally comprised of the following basic elements: a hollow barrel; a nozzle; a top fingergrip; a bottom fingergrip; a plunger; a handgrip.

The ergonomic syringe is typically used during catheterization procedures, where it is connected inline to a manifold, which in turn is connected to the catheter using tubing through which the dye is injected into the target blood vessels. The syringe, manifold, tubing and catheter are in fluid communication. The manifold, tubing and catheter are distinct elements separate from the syringe. Manipulation of the syringe by the operator causes the plunger to move longitudinally, in either a rearward or forward direction. Rearward plunger movement, towards the proximal end of the syringe, draws dye into the barrel from the manifold; forward plunger movement, towards the distal end of the syringe, expels dye into the manifold and therefrom into the catheter.

A hollow nozzle is located at the distal end of the barrel. The nozzle and barrel are in fluid communication, and the nozzle also may serve as a connector to a manifold and catheter, or other means of injecting dye.

Fingergrips are located on the exterior walls of the barrel, generally opposite each other, and include a top fingergrip and a bottom fingergrip.

The top fingergrip includes an open finger ring to contain an index finger, and an area which may be used to rest the index finger of the opposite hand, comprising an anterior top fingergrip and anterior top fingergrip catch. This top fingergrip design specifically enables, but does not require, use of two hands during dye injection. The bottom fingergrip includes an open interior bottom fingergrip, into which the third, fourth and little fingers of a hand may be inserted. The bottom fingergrip further includes an anterior bottom fingergrip around which the third, fourth and little fingers of the opposite hand may be placed, and a little finger rest which prevents the little finger of said hand from slipping off of the anterior bottom fingergrip. These features on this bottom fingergrip specifically enable, but do not require, use of two hands during dye injection and enable improved deployment of all fingers on one or both hands during the dye injection, enabling more force to be comfortably applied by the operator.

In an embodiment, (i) the top fingergrip is also placed such that the vertical plane of the rearmost interior wall of the finger ring is placed forward of the vertical plane of the rearmost interior wall of the interior bottom fingergrip, permitting more force to be exerted by the index finger during the injection, and (ii) the surface on which the third finger is placed is located forward of the surfaces on which the fourth and little fingers are placed, permitting more force to be exerted by the third finger during the injection. The barrel, nozzle and fingergrips are formed generally from a rigid material, and the nozzle, in an embodiment, may revolve around its longitudinal axis.

The plunger includes a plunger shaft, formed of a rigid material, and a plunger tip, formed of a generally resilient or elastomeric material. A barrel cap, located at the proximal end of the barrel, prevents the plunger from slipping out of the barrel when the plunger is moved proximally and may also be used to prevent the plunger from significantly rotating about its longitudinal axis.

The handgrip is located at the proximal end of the plunger and includes a handgrip base at the bottom, a handgrip arch in the middle, and a thumbrest and thumbhook at the top. The handgrip base extends significantly downward from the junction of the handgrip and the plunger, permitting a much greater surface area of the palm and ball of the thumb of the operator's hand to come in contact with the handgrip than in other manually-operated syringes. More particularly, the handgrip base extends, when being gripped by an operator, to the general area of the palmar surface of the annular ligament located at the base of the palm, and also is generally in contact with aspects of the flexor brevis pollicis, palmaris brevis, and abductor pollicis muscles of the hand; the handgrip arch is generally in contact with aspects of the adductor pollicis and immediately adjacent muscles of the hand.

The portion of the handgrip which includes the thumbrest and thumbhook extends upwards from the junction of the handgrip and plunger in generally the same axis as the other portions of the handgrip. The thumbrest enables use of the thumb on the hand opposite the hand gripping the interior bottom fingergrip to specifically enable, but not require, use of two hands during dye injection. The thumbhook provides a convenient means of moving the handgrip and plunger proximally, for purposes of drawing dye into the barrel from the manifold, using the thumb of the hand gripping the ergonomic syringe; alternatively, a finger from the opposite hand may be used to move the thumbhook. Additional features are included on the syringe to enhance its ergonomic performance, including surfaces on the handgrip and fingergrips sculpted to fit anatomical features on the operator's hand and fingers, and radii or bevels on corners and edges of gripping surfaces.

The ergonomic syringe therefore achieves its objects relative to the prior art, as follows:

(a) Increased comfort and reduced fatigue, strain and risk of disability compared to current syringes and the syringe described by Saez in U.S. Pat. No. 4,925,449 result from: (i) the flexibility of using either one or two hands to inject; (ii) the greatly increased surface area on the handgrip with which to exert force onto the plunger, and the shape and large surface area of the handgrip base, which distributes the pressure over a larger portion of the palm and ball of the thumb on the operator's hand, (iii) the locations of the fingergrips enable placement of fingers such that additional force may be applied without increasing operator discomfort. This object's achievement is particularly important as use of catheters sized 5 French and smaller increases.

(b) Easier injection of fluids during medical procedures is due to the increased comfort and reduced fatigue and strain for operators, and as a result of enabling one-handed operation for both loading the syringe with dye and injecting the dye; the thumbhook provides a convenient means of using the thumb on the hand gripping the syringe to draw back the syringe, permitting the other hand to be used for other purposes.

(c) Angiograms taken when the ergonomic syringe is used provide sufficient contrast because of the proper density of dye in the blood flow of the target vessels; this results from the operator being able to exert a larger amount of pressure to inject the dye without experiencing significant increase in discomfort, fatigue or strain compared to current manually-operated syringes and the syringe described by Saez in U.S. Pat. No. 4,925,449.

(d) The unit cost of the ergonomic syringe is expected to be similar to that of currently available syringes used for angiographic dye injections, less than that of the syringe described by Anwar in U.S. Pat. No 6,030,368, and far less expensive than using electro-mechanical injectors, in particular because the cost of the injector equipment is very high.

(e) The ergonomic syringe functions similarly to other manually-operated syringes used for angiography, in that (i) force is exerted directly upon a plunger, (ii) the barrel is positioned between the index and third fingers, (iii) the syringe is handheld, and (iv) the connection to the manifold and operation of the plunger with respect to loading and injecting are the same as with manually-operated angiography syringes.

BRIEF DESCRIPTION OF THE DRAWINGS

FIG. 4 is a perspective view of the invention.

FIG. 5 is another perspective view of the invention from the side opposite that shown in FIG. 4.

DETAILED DESCRIPTION OF THE INVENTION

An application of the ergonomic syringe is its use by an operator to inject dye into a patient during an angiographic procedure for the purpose of obtaining an angiogram showing the interior topography of blood vessels requiring evaluation. Although said ergonomic syringe may be used with a catheter of any size, it is particularly suited for use by an operator to inject dye through catheters sized 5 French or smaller, while increasing comfort and reducing the fatigue, strain, and risk of disability which may be associated with achieving the force required for such injections to achieve proper dye density in the blood flow through small catheters.

Referring to FIGS. 1–5, there is shown a preferred embodiment of the invention 10.

Figure 1:
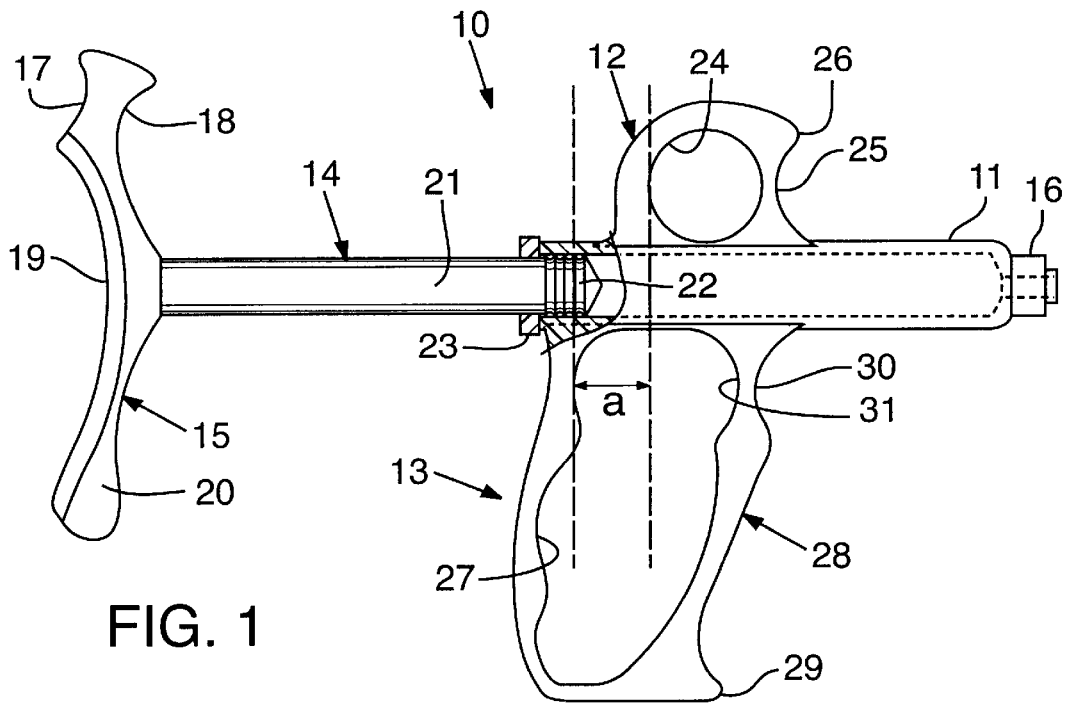
FIG. 1 is a side partial-section view of the invention.

FIG. 1 generally shows the ergonomic syringe 10, which includes the basic elements of a barrel 11, a top fingergrip 12, a bottom fingergrip 13, a plunger 14, and a handgrip 15. A hollow nozzle 16, in fluid communication with the cylindrical hollow barrel 11, is located on the distal end of said barrel 11. The nozzle 16 may be formed such that it rotates around its longitudinal axis. The proximal end of the barrel 11 is located at the end opposite the distal end. Said nozzle 16 may include a connector which may be a Luer-lock fitting and serves to connect the ergonomic syringe 10 to other catheterization equipment. Said catheterization equipment may include a manifold, tubing, a catheter and the like, where this catheterization equipment is separate from and not included as part of the ergonomic syringe 10.

A top fingergrip 12 is located on an outside wall of the barrel 11. A bottom fingergrip 13 is located on the outside wall of the barrel 11 generally opposite the top fingergrip 12. A plunger 14 includes a plunger shaft 21 and a plunger tip 22 where said plunger shaft 21 can slidably move forward and rearward within the lumen of the barrel 11 and where the plunger tip 22 fits snugly and sealingly within said lumen of the barrel 11. Upon rearward movement of the plunger 14, a vacuum is created within the lumen of the barrel 11, which, when in fluid communication through the nozzle 16 with a source of fluid draws said fluid into the lumen. Upon forward movement of the plunger 14, the fluid is expelled through the nozzle 16. A barrel cap 23 is located on the proximal end of the barrel 11, through which the plunger shaft 21 passes and which keeps said plunger from exiting the proximal opening of the barrel 11 when the plunger is moved rearward. The section of the plunger shaft 21 fits within the shape of the opening of the barrel cap 23 through which it passes, where the fit of said section in the opening of the barrel cap 23 does not permit significant rotation around the longitudinal axis of the plunger shaft 21. A handgrip 15 is located on the proximal end of the plunger 14, where the handgrip base 20 extends significantly downward from the junction of the plunger shaft 21 and the handgrip 15, and where the portion of the handgrip 15 including the thumbrest 17 and thumbhook 18 extend significantly upwards from the junction of the plunger shaft 21 and the handgrip 15.

The top fingergrip 12 includes an open finger ring 24, an anterior top fingergrip catch 26 and an anterior top fingergrip 25. The anterior top fingergrip 25 is shaped to accept placement of the index finger of the hand opposite the hand gripping the interior bottom fingergrip 27. The anterior top fingergrip catch 26 is located above the anterior top fingergrip 25 and at the top of the top finger grip 12, and prevents said index finger from slipping off of the top fingergrip 12 during an injection.

The finger ring 24 is open, to accept the index finger of the hand gripping the bottom fingergrip 13. The opening of the finger ring 24 is sufficient to accept an index finger the hand of which has on it at least one surgical glove. The interior front wall of the finger ring 24 also provides a surface for the comfortable placement of the index finger of the hand gripping the interior bottom fingergrip 27 when dye is being drawn into the barrel 11 using the thumb of said hand to manipulate the thumbhook 18, where said thumb and said index finger are exerting force in opposite directions against surfaces to move the plunger 14 rearward. The top fingergrip 12 may be placed such that the vertical plane of the rearmost interior wall of the finger ring 24 is placed forward of the vertical plane of the topmost portion of the rearmost wall of the interior bottom fingergrip 27, where the distance between said planes is designated as "a" in FIG. 1. This placement of the fingergrips permits more force to be comfortably exerted by muscular contraction of the hand and index finger during the injection.

The bottom fingergrip 13 includes an open interior bottom fingergrip 27, an anterior bottom fingergrip 28, and a third finger notch 31. The anterior bottom fingergrip 28 includes a little finger rest 29 and a third finger rest 30. The opening of the interior bottom fingergrip 27 is sufficient to accept fingers of a hand wearing at least one surgical glove. The surface of the rear wall of the interior bottom fingergrip 27 is formed to create surfaces to accept placement of the third, fourth and little fingers of the hand gripping the interior bottom fingergrip 27. The surface of the rear wall of the interior bottom fingergrip 27 on which the third finger is placed is located forward of the surfaces of said rear wall on which the fourth and little fingers are placed, permitting more force to be comfortably exerted by the third and fourth fingers during the injection. The third finger notch 31 provides a comfortable placement of the third finger of the hand gripping the interior bottom fingergrip 27 when dye is being drawn into the barrel using the thumb of said hand to manipulate the thumbhook 18, where the thumb and third finger are exerting force in opposite directions against surfaces to move the plunger 14 rearward.

The bottom fingergrip 13 further includes an anterior bottom fingergrip 28 around the front surface of which the third, fourth and little fingers of the hand opposite that which grips the interior bottom fingergrip 27 may be placed, a little finger rest 29 which prevents the little finger of said hand from slipping off of the anterior bottom fingergrip 28, and a third finger rest 30 which provides a comfortable placement of the third finger during injection. The surface contours of the interior bottom fingergrip 27 and anterior bottom fingergrip 28 provide increased surface area and features which enable a more secure grip when applying force during injection, and the option of using either one or two hands comfortably.

The plunger 14 includes a plunger shaft 21 and plunger tip 22 where said plunger shaft 21 slides forward or rearward within the lumen of the barrel 11. Such movement is created by the operator's application of force to either the rearmost surface of the handgrip 15 or on the foremost surface of the thumbhook 18, both of which are located on the handgrip 15. The plunger tip 22 may be formed of a resilient or elastomeric material.

The handgrip 15 is located on the proximal end of the plunger 14 and includes a thumbrest 17, a thumbhook 18, a handgrip arch 19, and a handgrip base 20. The handgrip arch 19 and handgrip base 20 contact the ball of the thumb 33 and palm of the hand 34 of the operator as shown in FIG. 4; together these members provide a much greater surface area on which to distribute the force exerted by the operator during injection, thereby decreasing discomfort, strain and fatigue. When the operator uses two hands to inject, the tip of the thumb of the hand opposite that gripping the interior bottom fingergrip 27 may be used to exert additional forward pressure onto the handgrip 15 and therefrom onto the plunger 14 by placing said thumb onto the thumbrest 17 and pressing forward. The thumbrest 17 is angled forward to provide a surface the plane of which generally corresponds to the plane of the surface of the thumb which presses forward upon it.

The thumbhook 18 may be used by the operator to pull dye into the ergonomic syringe 10, by placing the thumb of the hand gripping the interior bottom fingergrip 27 onto the thumbhook 18 and applying force to push it rearward, which in turn moves the plunger 14 rearward. Upon rearward movement of the plunger 14, a vacuum is created within the lumen of the barrel 11, which, when in fluid communication through the nozzle 16 with a source of fluid draws said fluid into the lumen. A barrel cap 23 is located on the proximal end of the barrel 11, through which the plunger shaft 21 passes and which keeps said plunger from exiting the proximal opening of the barrel 11 when the plunger 14 is moved rearward. Alternatively, the operator may use a finger from the hand opposite that gripping the ergonomic syringe 10 to grip the thumbhook 18 to pull the plunger 14 rearward.

Figure 2A:
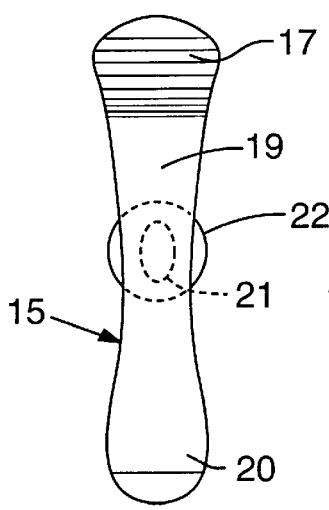
FIG. 2A is a back view of the invention.
Figure 2B:
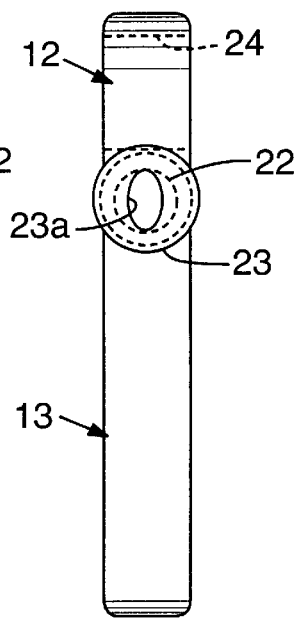
FIG. 2B is another back view of the invention.

FIG. 2A shows a back view of the handgrip 15, plunger shaft 21 and plunger tip 22. A section of the plunger shaft 21 is shown, in phantom, generally as an oval, to fit a corresponding oval shape of barrel cap opening 23a, as shown in FIG. 2B, through which it passes into the lumen of the barrel 11. The matching shapes of the plunger shaft 21 and barrel cap opening 23a substantially limit the amount of rotation of the plunger shaft 21 about its longitudinal axis. The handgrip base 20 is flared at the bottom to provide an ergonomically advantageous shape to fit the ball of the thumb 33 and palm of the hand 34 of the operator, as shown in FIG. 4, where either hand may be used to grip the ergonomic syringe 10. Alternative section shapes of the plunger shaft 21 and the corresponding barrel cap opening 23a may be used to limit the rotation of the plunger shaft 21 about its longitudinal axis.

FIG. 2B shows a back view of the barrel 11, top fingergrip 12, bottom fingergrip 13, the barrel cap 23 and the barrel cap opening 23a. The interior and exterior surfaces of the sidewall of the barrel 11, and the plunger tip 22 are shown in phantom.

Figure 3:
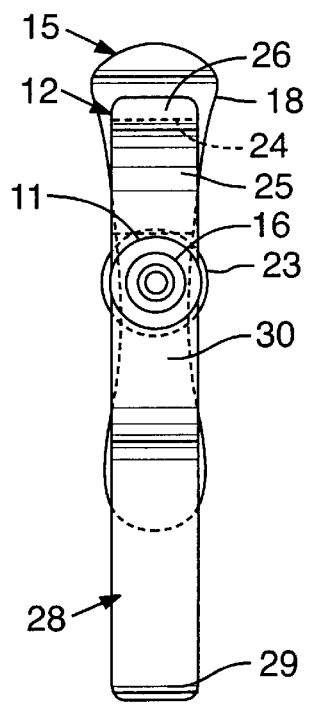
FIG. 3 is a front view of the invention.

FIG. 3 shows a front view of the ergonomic syringe 10. The top fingergrip 12 and bottom fingergrip 13 provide sufficient surface area for comfortable gripping by the operator using either one or two hands. FIG. 3 shows the widths of the top fingergrip 12 and bottom fingergrip 13 as somewhat less than the maximum diameter of the barrel 11; said widths may also be wider or narrower relative to the barrel 11 than shown in FIG. 3 without departing from the intent of the invention.

FIG. 4 shows a perspective view of the ergonomic syringe 10 held in a fashion intended for one-handed use, and illustrates the positioning of the handgrip 15 against the ball of the thumb 33 and palm of the hand 34. This FIG. 4 also shows the operator's hand in phantom, and the edges and corners of the ergonomic syringe 10 as having radii or bevels to increase comfort to the operator while performing injections. The third, fourth and little fingers grip the interior bottom fingergrip 27. The index finger passes through the finger ring 24 to grip the top fingergrip 12. The handgrip arch 19 is pressed generally against the ball of the thumb 33 and palm of the hand 34, generally including aspects of the adductor pollicis muscle and adjacent muscles of the hand. The handgrip base 20 presses generally onto the area of the base of the palm, generally including the area of the palmar surface of the annular ligament located at the base of the palm and aspects of the flexor brevis pollicis, palmaris brevis, and abductor pollicis muscles of the hand. The surface area of the handgrip 15 contacting the ball of the thumb 33 and the palm of the hand 34 is much greater than with any other handheld syringes in current use or described in the prior art. By squeezing the fingers towards the palm of the hand 34, forward pressure is exerted onto the handgrip 15 and therefrom onto the plunger 14, causing the plunger to move forward thereby expelling dye from the ergonomic syringe 10. Although FIG. 4 shows the right hand gripping the ergonomic syringe 10, it may be used in one-handed fashion in either hand.

FIG. 5 shows a perspective view of the ergonomic syringe 10 held in a fashion intended for two-handed use. The hand gripping the interior bottom fingergrip 27 does so generally in the same fashion as shown in FIG. 4. The third, fourth and little fingers of the opposite hand wrap around and grip the anterior bottom fingergrip 28, with the third finger placed against the third finger rest 30 and the little finger placed just above the little finger rest 29. The palm of said opposite hand is placed over the third, fourth and little fingers of the hand gripping the interior bottom fingergrip 27. The index finger of the opposite hand wraps around the anterior top fingergrip 25, where, during injection, it is helped to stay in place by the anterior top fingergrip catch 26. The thumb of the opposite hand is placed against the thumbrest 17. By squeezing all of the fingers and the thumb of said opposite hand together, in concert with the hand gripping the interior bottom fingergrip 27 forward pressure is applied onto the handgrip 15 and therefrom onto the plunger 14 causing the plunger 14 to move forward thereby expelling dye from the barrel 11 and through the nozzle 16 of the ergonomic syringe 10.

In another embodiment, the ergonomic syringe 10 may have surfaces of certain members treated or have applied to them materials which modify the coefficient of friction of said surfaces, or which provide a resilient or yielding surface. For example, portions of the top fingergrip 12, bottom fingergrip 13, thumbrest 17, thumbhook 18, handgrip arch 19 and handgrip base 20 may have such treatment or material application to provide additional comfort and prevent slippage when using the ergonomic syringe 10.

Figure 6:
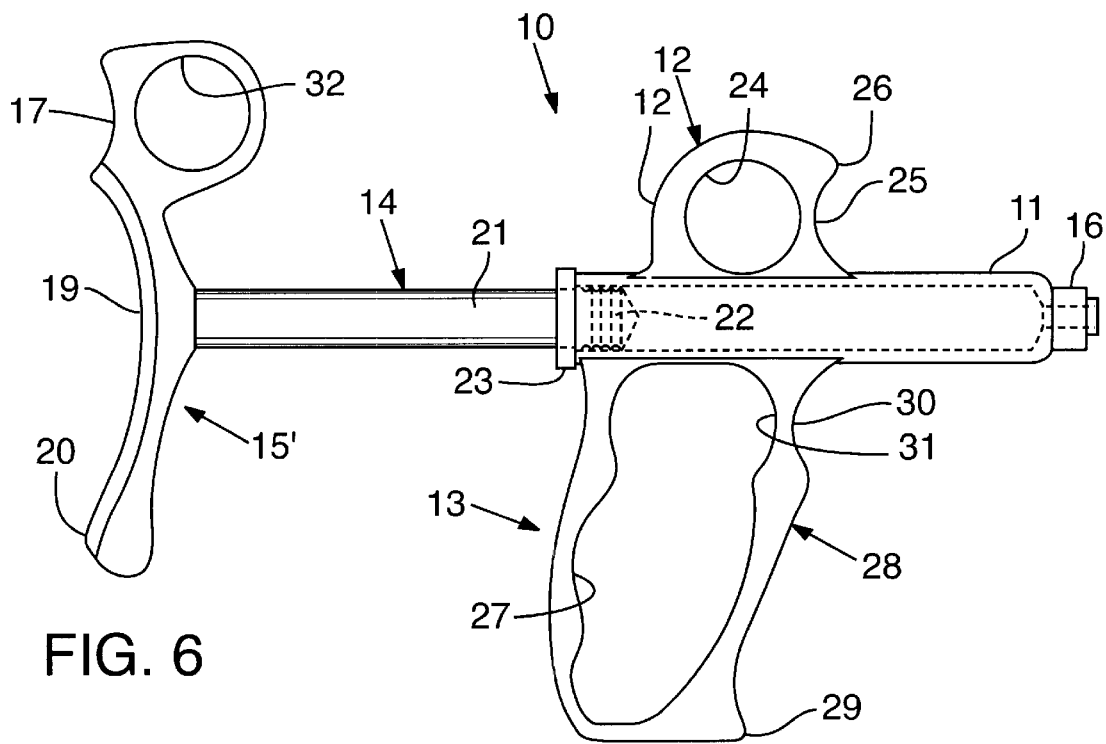
FIG. 6 is a side view of an alternative feature of the invention.

FIG. 6 shows another embodiment, wherein the ergonomic syringe 10 has a thumbring 32 substituted for the portion of the handgrip 15' comprising the thumbhook 18 shown in a prior embodiment of this invention. Said thumbring 32 provides a means of manipulating the handgrip 15' and plunger 14 using the thumb of the hand gripping the interior bottom fingergrip 27, whereby such manipulation is similar to that of currently-used syringes having a ring on the plunger head.

This detailed description of the invention is for illustrative purposes only. A reading by those skilled in the art will bring to mind various changes without departing from the spirit and scope of the invention.

We claim:

1. An ergonomic syringe to be used for injecting fluids under pressure in medical procedures, including angiographic procedures, which includes:
   a) a generally cylindrical hollow barrel having a nozzle at its distal end and a generally open proximal end;
   b) a top fingergrip located on an outside wall of said barrel, said top fingergrip having an open finger ring into which an operator may insert a single finger for the purpose of gripping said ergonomic syringe;
   c) a bottom fingergrip located on an outside wall of the barrel generally opposite the wall on which the top fingergrip is located, said bottom fingergrip having an open interior bottom fingergrip into which an operator may insert more than one finger for the purpose of gripping the ergonomic syringe;
   d) a plunger having a plunger shaft including a distal end and a proximal end, said distal end being received into the proximal end of the barrel where said plunger may slidably move forward and rearward inside the lumen of the barrel;
   e) a handgrip located on the proximal end of the plunger, said handgrip including:
      (i) a handgrip arch located on the proximal side of the handgrip generally opposite the point at which the handgrip joins the plunger, said handgrip arch shaped generally in a curve to fit a portion of the palm of an operator's hand and ball of the operator's thumb including a significant area of the adductor pollicis muscle;
      (ii) a handgrip base extending away from the handgrip arch, said handgrip base being formed as an elongate finger generally shaped to fit a significant part of the lower portion of the palm of an operator's hand and ball of the operator's thumb generally including an area distal to the palmar surface of the annular ligament of the hand;
      (iii) a thumbgrip extending away from the point at which the handgrip joins the plunger in a direction generally opposite that of the handgrip base.

2. The ergonomic syringe of claim (1), wherein:
   a) the top fingergrip further including an anterior top fingergrip and anterior top fingergrip catch, the purpose of which is to provide a resting place for and to restrain from moving during injection a finger of the operator's hand opposite that which grips the interior bottom fingergrip;
   b) the plunger further including a plunger tip which fits snugly and sealingly within the lumen of the barrel;
   c) the bottom fingergrip further including an anterior bottom fingergrip providing a feature which the operator may grip using more than one finger of the hand opposite the hand gripping the interior bottom fingergrip, said anterior bottom fingergrip being located on the distal surface of the front wall of the bottom fingergrip and including:
      (i) a little finger rest located generally at the bottom of the anterior bottom fingergrip;
      (ii) a third finger rest, located generally at the top of the anterior bottom fingergrip;
   d) the handgrip further including on the portion of the handgrip extending away from the point at which the handgrip joins the plunger and in a direction generally opposite that of the handgrip base, one selected from the group comprising:
      (i) a thumbhook located generally opposite the thumbrest and on the distal surface of the handgrip;
      (ii) a thumbring located generally opposite the thumbrest and on the distal surface of the handgrip.

3. The ergonomic syringe of claim (1) wherein a vertical plane of a rearmost wall of the finger ring is forward of a vertical plane of a topmost portion of a rearmost wall of the interior bottom fingergrip, where a third finger is placed.

4. The ergonomic syringe of claim (1) wherein a vertical plane of a topmost portion of a rearmost wall of the interior bottom fingergrip where a third finger is placed is forward of the bottom portions of the interior bottom fingergrip where the fourth and little fingers are placed.

5. The ergonomic syringe of claim (1) which further includes a barrel cap located at the proximal end of the barrel through which said plunger shaft passes, the purpose of which is to retain the plunger within the barrel when the plunger is moved rearwards;
   said barrel cap having an opening through which the plunger shaft passes;
   the plunger shaft having an irregular section;
   the shape of said opening being generally similar to said section of the plunger shaft, so that rotation of the plunger shaft about its longitudinal axis is substantially prevented.

6. The ergonomic syringe of claim (2) wherein the vertical plane of the rearmost wall of the finger ring is forward of the vertical plane of the topmost portion of the rearmost wall of the interior bottom fingergrip.

7. The ergonomic syringe of claim (2) wherein the vertical plane of the topmost portion of the rearmost wall of the interior bottom fingergrip where a third finger is placed is forward of the bottom portions of the interior bottom fingergrip where the fourth and little fingers are placed.

8. The ergonomic syringe of claim (2) which further includes a barrel cap located at the proximal end of the barrel through which the plunger shaft passes, the purpose of which is to retain the plunger within the barrel when the plunger is moved rearwards;
   said barrel cap having an opening through which the plunger shaft passes;
   the plunger shaft having an irregular section;
   the shape of said opening being generally similar to said section of the plunger shaft, so that rotation of the plunger shaft about its longitudinal axis is substantially prevented.

9. The ergonomic syringe of claim (1) wherein portions of the surfaces of said ergonomic syringe are modified by one or more means selected from the group comprising incorporation of a different material, overmolding using a different material, a surface treatment, a surface texture, and a coating;
   said portions of the surfaces thereby having a different coefficient of friction and a more resilient consistency than the surfaces of other portions of the ergonomic syringe not so modified.

* * * * *